US011445901B2

(12) United States Patent
Moein et al.

(10) Patent No.: US 11,445,901 B2
(45) Date of Patent: Sep. 20, 2022

(54) ONE-TIME USE EXPANDABLE SPECULUM

(71) Applicants: Sudabeh Moein, San Diego, CA (US); Lawrence Benjamin Fischel, Roseville, CA (US)

(72) Inventors: Sudabeh Moein, San Diego, CA (US); Lawrence Benjamin Fischel, Roseville, CA (US)

(73) Assignee: THE MOEIN FAMILY TRUST, San Diego, CA (US)

( * ) Notice: Subject to any disclaimer, the term of this patent is extended or adjusted under 35 U.S.C. 154(b) by 177 days.

(21) Appl. No.: 16/538,532

(22) Filed: Aug. 12, 2019

(65) Prior Publication Data

US 2020/0046216 A1 Feb. 13, 2020

Related U.S. Application Data

(60) Provisional application No. 62/717,338, filed on Aug. 10, 2018.

(51) Int. Cl.
*A61B 1/303* (2006.01)
*A61B 1/32* (2006.01)
*A61M 29/02* (2006.01)
*A61B 17/00* (2006.01)
*A61B 1/06* (2006.01)

(52) U.S. Cl.
CPC ............. *A61B 1/303* (2013.01); *A61B 1/32* (2013.01); *A61M 29/02* (2013.01); *A61B 1/06* (2013.01); *A61B 2017/00557* (2013.01)

(58) Field of Classification Search
CPC . A61B 1/303; A61B 1/32; A61B 2017/00557; A61M 29/02
See application file for complete search history.

(56) References Cited

U.S. PATENT DOCUMENTS 4,984,564 A * 1/1991 Yuen ................... A61B 17/0293
600/207
5,342,385 A * 8/1994 Norelli ................... A61B 17/02
604/104

(Continued)

FOREIGN PATENT DOCUMENTS

AU 2006292818 B2 10/2012
EP 190014 B1 3/1994

(Continued)

OTHER PUBLICATIONS

International Search Report and Written Opinion issued in International Patent Application No. PCT/US2019/46197, dated Nov. 1, 2019 (Nov. 1, 2019). 9 pages.

*Primary Examiner* — Kevin T Truong
*Assistant Examiner* — Tracy L Kamikawa
(74) *Attorney, Agent, or Firm* — Mintz, Levin, Cohn, Ferris, Glovsky and Popeo, P.C.

(57) ABSTRACT

Expandable specula devices and methods are disclosed. In one aspect, a speculum includes inner and outer balloon layers configured to expand circumferentially. The inner and outer balloon layers form a sealed cavity configured to hold a liquid. The speculum further includes an access tube for injecting the liquid into the cavity. The speculum further includes a shape memory alloy layer within the outer balloon layer. The shape memory alloy layer is configured to transition to a first shape when heated above a transition temperature.

16 Claims, 5 Drawing Sheets

(56) References Cited

U.S. PATENT DOCUMENTS

| | | | |
|---|---|---|---|
| 5,716,329 A | 2/1998 | Dieter | |
| 8,608,652 B2 | 12/2013 | Voegele et al. | |
| 8,690,817 B2 * | 4/2014 | Assaf | A61M 27/002 |
| | | | 604/8 |
| 9,017,253 B2 * | 4/2015 | Guralnik | A61B 17/0218 |
| | | | 600/208 |
| 9,259,233 B2 * | 2/2016 | Gruber | A61B 17/12136 |
| 9,907,544 B2 | 3/2018 | Nadershahi et al. | |
| 10,058,240 B2 | 8/2018 | Alexander et al. | |
| 10,064,651 B2 | 9/2018 | Norred et al. | |
| 2007/0225744 A1 * | 9/2007 | Nobles | A61M 29/02 |
| | | | 606/192 |
| 2007/0270898 A1 | 11/2007 | Lillehei | |
| 2009/0143649 A1 | 6/2009 | Rossi | |
| 2014/0018732 A1 | 1/2014 | Bagaoisan et al. | |
| 2015/0250465 A1 * | 9/2015 | Kaiser | A61B 17/025 |
| | | | 606/90 |
| 2016/0287063 A1 | 10/2016 | Ramanujam et al. | |
| 2018/0071502 A1 * | 3/2018 | Hakim | A61B 17/52 |
| 2018/0289934 A1 * | 10/2018 | Niazi | A61M 25/1002 |

FOREIGN PATENT DOCUMENTS

| | | | | |
|---|---|---|---|---|
| EP | 2627270 B1 | 12/2017 | | |
| GB | 2536869 A | 10/2016 | | |
| JP | 5911083 B2 | 4/2016 | | |
| WO | WO-2017214069 A1 * | 12/2017 | | A61B 17/12036 |

* cited by examiner

ONE-TIME USE EXPANDABLE SPECULUM

CROSS-REFERENCE TO RELATED APPLICATIONS

The present application claims priority to U.S. Patent Application No. 62/717,338, filed Aug. 10, 2018, entitled EXPANDABLE SPECULUM, the disclosure of which is incorporated herein by reference in its entirety.

FIELD

One-time use, expandable specula and associated methods are disclosed herein.

BACKGROUND

Health care providers employ specula (speculums) for pelvic examinations and treatment. For example, physicians use specula when screening for cervical cancer and sexually transmitted diseases (STDs). Specula are also used when evaluating patients for pain, bleeding and discharge. Such examinations and treatments are important for maintaining women's health and prevention of cancer.

Every two minutes a woman dies from cervical cancer. Over 80% of these women are from low to middle income countries. One of the major motivations for the disclosed technology is to provide a more practical screening tool for these women, in helping our mission to improve the screening and treatment of cervical cancer. Cervical cancer often results from infection by human papilloma virus (HPV), a communicable disease that is easily communicated between humans, or from inanimate object to humans. Medical equipment, including specula, may not be sufficiently cleaned or sterilized between patients, resulting in the spread of HPV, human immunodeficiency virus (HIV), other viruses, microbes, and other source of disease, from one patient to another.

Traditional specula include an anterior blade and a posterior blade, which push the anterior and posterior vaginal walls out of the field of view of a clinician during a pelvic examination or treatment. However, traditional billed specula do not retract vaginal walls laterally. This causes visualization problems when examining multiparous patients, obese patients, patients with a redundant vaginal wall, and patients with pelvic organ prolapse. The examiner will have a difficult time visualizing the cervix or gaining easy access to the cervix during examination and treatment, creating technical difficulties for the clinician, and pain and embarrassment for the patient. Moreover, traditional specula used throughout the world are made of metal or hard plastic.

In a colposcopy clinic, among other options, the most common treatment for cervical pre-cancers is a loop electrosurgical excision procedure (LEEP), which involves using a hot wire loop to excise part of the cervix. This procedure cannot be done using a metal speculum. A specially coated speculum is used during this procedure which is costly. Additionally, during this procedure, lack of retraction of the lateral vaginal walls due to the shape of the current speculums poses great difficulty on the physician during the procedure.

Moreover, traditional double billed specula may be painful and uncomfortable for patients, as they may be cold, rigid, large, and click during use. Such discomfort may cause some patients to avoid examinations, resulting in undetected and therefore untreated infections or conditions. After age 40, women often have prolapsed vaginal walls, which partially blocks the view of the health provider. This is often exacerbated by obesity. Therefore, there is a need for a speculum that enables a better view, that does not transmit infection, that is not painful, and that is comfortable for patients.

SUMMARY

Aspects of the current subject matter relate to a speculum. The speculum includes an outer balloon layer configured to expand circumferentially. The speculum includes an inner balloon layer configured to expand circumferentially. The inner balloon layer is formed within the outer balloon layer. The outer balloon layer and the inner balloon layer form a sealed cavity configured to hold a liquid. The speculum further includes an access tube for injecting the liquid into the cavity. The speculum further includes a shape memory alloy layer within the outer balloon layer configured to transition to a first shape when heated above a transition temperature.

In some variations one or more of the following features can optionally be included in any feasible combination. For example, at least a portion of the inner balloon layer may be translucent. The shape memory alloy may comprise nitinol. The inner balloon layer may have a more rigid structure than the outer balloon layer. The outer balloon layer may comprise latex, rubber, silicon, or a flexible plastic. The speculum may further includes rods incorporated into the outer balloon wall in a longitudinal direction. The rods may be flexible. The rods may comprise silicon. The shape memory alloy layer may comprise a mesh. The shape memory alloy layer may abut the inner balloon layer. The shape memory alloy layer may surround the inner balloon layer. The inner balloon layer may surround the shape memory alloy layer. The outer balloon layer may surround the shape memory alloy layer. The outer balloon layer may abut the shape memory alloy layer. The speculum may further include an applicator configured to insert the speculum into a vaginal canal. The speculum may further include a valve to regulate a flow of fluid from a syringe into the access tube.

The details of one or more variations of the subject matter described herein are set forth in the accompanying drawings and the description below. Other features and advantages of the subject matter described herein will be apparent from the description and drawings, and from the claims.

BRIEF DESCRIPTION OF THE DRAWINGS

FIG. 4A is a cross section of an expandable balloon speculum with an outer balloon layer surrounding an inner balloon layer. The inner balloon layer surrounds and abuts a shape memory alloy mesh layer.

FIG. 4B is a cross section of an expandable balloon speculum with an outer balloon layer surrounding a shape memory alloy mesh layer. The shape memory alloy mesh layer surrounds and abuts the inner balloon layer.

FIG. 4C is a cross section of an expandable balloon speculum with an outer balloon layer abutting and surrounding a shape memory alloy mesh layer. The shape memory alloy mesh layer surrounds an inner balloon layer.

FIG. 4D is a cross section of an expandable balloon speculum with an outer balloon layer surrounding a shape memory alloy mesh layer. The shape memory alloy mesh layer surrounds the inner balloon layer. The shape memory alloy mesh layer is between but does not abut either the inner balloon layer or the outer balloon layer.

FIG. 5 illustrates a specula with a cross section corresponding to FIG. 4B, since the mesh would be further obscured in perspectives of specula corresponding to the cross sections of FIGS. 4A, 4C, and 4D by the inner balloon layer.

DETAILED DESCRIPTION

Figure 1:
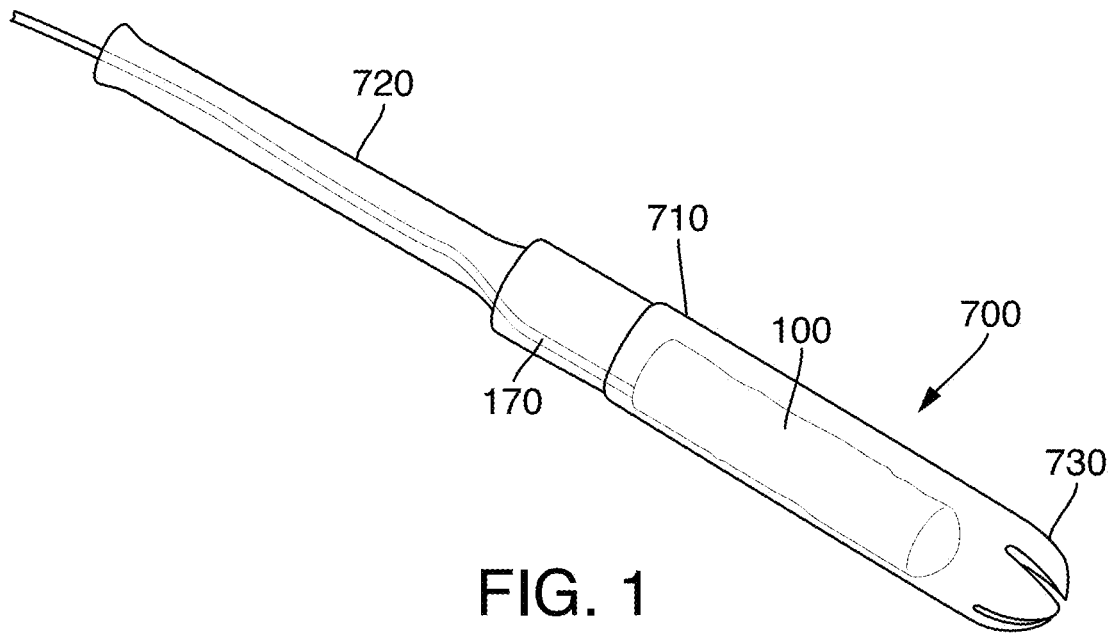
FIG. 1 depicts an expandable balloon speculum inside an applicator for inserting the speculum into the vaginal canal of a patient.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments. The features illustrated or described in connection with one exemplary embodiment may be combined with the features of other embodiments. Such modifications and variations are intended to be included within the scope of the present disclosure.

Specula are for a wide range of examination procedures, including general pelvic exam, screening for pelvic infections, cervical cancer screening, screening for vaginal bleeding, any cancer of the female pelvis, pelvic organ prolapse, colposcopy, any gynecological procedure that mandates biopsy or sampling of the internal pelvic organs, endometrial biopsy. In addition to examinations, specula are used for a wide range of surgical procedures and in office treatments, including vaginal hysterectomy, loop electrosurgical excision procedure (LEEP), endometrial ablation, vaginal hysterectomy, hysteroscopy, polypectomy, and in vitro fertilization procedures.

Traditional specula have upper and lower bills that apply upward and downward pressure to a patient's vaginal canal to open a viewing and examination pathway for pelvic examination and treatment. Unlike double billed specula, expandable balloon specula may be inserted using an applicator, similar to insertion of a tampon, before the balloon specula expands.

With traditional specula, surgeons have to be very careful to avoid contact between metal blades and hot wire loops or cautery tips, as metal blades may conduct heat and burn a patient. Unlike metal billed specula, expandable balloon specula feature an inner balloon layer that does not conduct heat, reducing the possibility of inadvertently burning a patient.

The balloon specula may include inner and outer balloon layers that are sealed, with a cavity between the balloon layers that may be filled with a fluid or gas, causing the balloon to expand. The balloon speculum may be an annular balloon that is smoothly expandable so as to apply an outwardly-directed radial force against the vaginal soft tissue in equal distribution from the vaginal introitus (opening) all the way to the end of the patient's vagina where the cervix is found. The inner and outer annular balloon walls are made of a flexible resilient material with elastic properties to permit expansion of the vaginal wall in a circumferential manner. In various embodiments, the expandable balloon spectrum may include baffles to support this circumferential expansion. In various embodiments, the expansion may be substantially uniform. In various embodiments, the expansion may be non-uniform due to, for example, the shape of a patient's vaginal canal or the design of a speculum.

The inner balloon layer may have a more rigid structure than the outer balloon layer. The rigid structure may prevent the speculum from folding in upon itself and maintain a tubular shaped lumen during examination and treatment. This is particularly useful during the examination of a patients with vaginal wall prolapse.

The balloon can be filled with fluid like water, normal saline, or a chemiluminescent fluid. The chemiluminescent fluid not only helps in expending the balloon walls but also functions as a light source directly in the vagina, therefore eliminating the need for an outside light source which typically requires electricity. This is particularly useful in the low to middle income countries where access to electricity may be a challenge.

The light emitted by a chemiluminescent fluid may be of a color, or contain wavelengths, to assist with particular examinations or screenings.

The expandable balloon speculum may also include a shape memory alloy mesh layer, which expands when heated by the body heat from a patients vaginal canal.

The shape memory alloy mesh layer may be within the inner balloon layer and abutting the inner balloon layer, or between the inner and outer balloon layer. Shape memory alloy mesh layers that are between the inner and outer balloon layer may abut the inner balloon layer, abut the outer balloon layer, or not abut either layer, when the balloon speculum is expanded. Two layers abut when they are either in direct contact, are affixed to one another, or in manufacturing are integrated with one another.

After the expandable balloon speculum is inserted into a patient's vaginal canal, it expands due to shape memory alloy heating, or pressure exerted by fluid injected between the inner and outer layers via an input tube. Once expanded, a lumen having a tubular shape, within the inner balloon layer, affords a channel for examination and treatment.

Ambient lighting is generally not sufficient for an examination. In various embodiments, a chemiluminescent fluid fills at least a portion of the cavity between the inner and outer balloon layers. In various embodiments, at least a portion of the expandable balloon lumen is sufficiently translucent for light emitted by the chemiluminescent fluid to illuminate the vaginal canal and/or cervix of a patient. In various embodiments, the chemiluminescent fluid fills a component separate from the speculum. For example, the chemiluminescent fluid may fill a tube or rod that may be inserted into the lumen of the speculum to illuminate the vaginal canal.

The specula described herein have certain advantages over traditional specula.

A first advantage, in some embodiments, is that the specula are for one time use, so that each speculum may be unwrapped and sterile for each use, thereby preventing the spread of HPV, HIV, microbes, viruses, or other infective agents.

A second advantage, in some embodiments, is that the specula are balloon specula that expand circumferentially after insertion into the vaginal canal. As a result, smaller specula, for example, the size of a tampon, with a diameter of 1 cm-2 cm, may be inserted into the vaginal canal. The balloon speculum may then be gently inflated or expanded to a circumference sufficient for a health care provider to perform an examination. This allows for insertion of a smaller speculum than a traditional speculum.

A third advantage, in some embodiments, is that the specula expand and apply pressure to the vaginal walls circumferentially, as opposed to traditional specula that apply pressure using the top and bottom bills of a speculum. The circumferential pressure is applied all around the canal, including laterally, instead of just above and below the speculum. This improves the pressure distribution within the vaginal canal during examination. The balloon speculum may be expanded gradually and more comfortably for the patient.

A fourth advantage, in some embodiments, is that the specula do not "click" or make the clicking noise associated with traditional specula, because the specula described herein expand circumferentially, and do not rely on mechanical opening of bills.

A fifth advantage, in some embodiments, is that the specula may be inserted with a tampon-like applicator, which allows the balloon's tip to touch the cervix which is located at the distal end of the vaginal canal, and then the applicator may be withdrawn. This allows for more comfortable and proper placement of the balloon speculum prior to its expansion. This process may be significantly more comfortable for a patient than insertion and placement of a double billed speculum, which often requires moving the double billed speculum, with open blades, back and forth to find the cervix.

A sixth advantage, in some embodiments, is that the specula have a continuous exterior surface and no bills. This decreases the possibility of pinching tissue, or catching hair, further increasing comfort for the patient.

A seventh advantage, in some embodiments, is that the specula have an outer balloon layer formed of a smooth, soft surface, such as a latex, rubber, silicon, or flexible plastic, which may be more comfortable than traditional specula with more rigid, and possibly cold, surfaces.

An eighth advantage, in some embodiments, is that the specula are at least partially filled with a chemiluminescent (CI) fluid that provides illumination once the speculum is inserted into the vaginal canal. This enables the physician to see, for example, the patient's vagina, cervix or other anatomical detail during a pelvic examination or treatment. This obviates the need to rely on a lamp or handheld light source, such as a flashlight.

An ninth advantage, in some embodiments, is that the specula include a mesh, layer, bars, or other structural elements formed of a shape memory alloy, such as the nickel titanium alloy nitinol. Nitinol exhibits a shape memory effect, and has superelastic properties. These properties make it possible to, for example, introduce a "compressed" mesh into a speculum into a vaginal canal, but once nitinol warms through the transformation temperature from being inside the vaginal canal, the speculum may expand to the undeformed, expanded mesh shape.

A tenth advantage, in some embodiments, is that the specula provide a better view for the health care provider than is possible with traditional specula, particularly for patients with a pelvic organ prolapse, and/or who are obese, because the prolapsed vaginal walls are prevented from encroaching on the viewing area by prolapsing through the lateral sides of open blades.

FIG. 1 depicts an expandable balloon speculum 100 inside an applicator 700 for inserting the speculum 100 into the vaginal canal of a patient. The applicator 700 includes a chamber 710 that houses a speculum 100, a plunger 720 that, once depressed, projects the speculum 100 out of the chamber 710 through the tip 730 of the applicator 700. The exterior of the chamber 710 may be formed of cardboard or plastic, similar to materials used in tampon applicators, to facilitate insertion of the deflated balloon speculum. An access tube 170 to inject fluid into the speculum 100 may extend from speculum 100. The diameter of the applicator 700 may vary based on the size of the vaginal canal of the patient. For example, the applicator 700 may have a diameter of about 0.5 cm to about 2 cm. The length of the applicator may be about 10 cm to about 20 cm.

In various embodiments, the expandable speculum may include thin semiflexible rods incorporated into the outer balloon wall in a longitudinal fashion. The rods may be formed of silicon, or another flexible material. The rods may be arrayed in parallel, and in close proximity to each other, to allow for consistency in the shape and elasticity of the deflated speculum to facilitate insertion of a deflated balloon speculum into the vaginal canal. When the applicator deploys the unexpanded speculum in to the vagina, retraction of the applicator will not cause the balloon speculum to collapse or get stuck in a corner of the vaginal wall.

Figure 2:
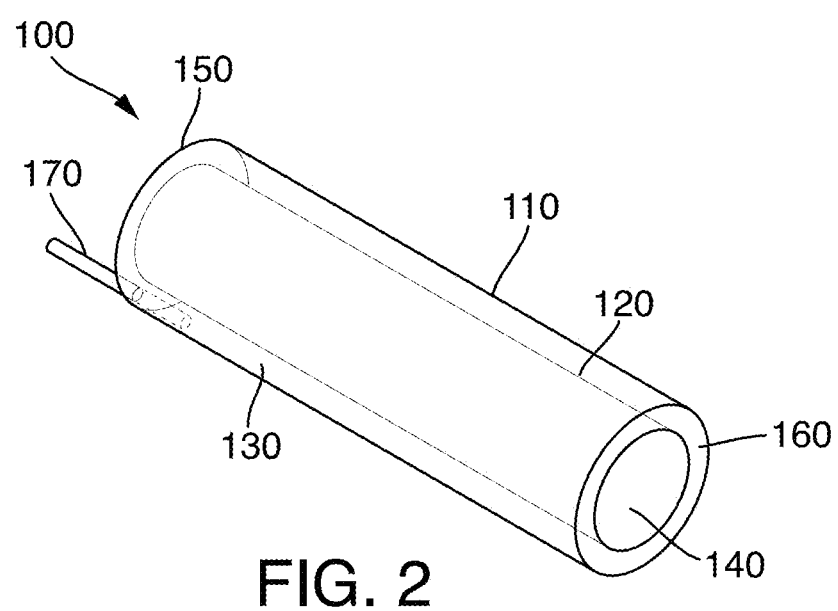
FIG. 2 depicts an expandable balloon speculum, with a tube insertion site for inserting fluid between the inner and outer layers of the balloon speculum to expand the speculum circumferentially.

FIG. 2 depicts an expandable balloon speculum 100. The balloon speculum 100 includes an outer balloon layer 110 and an inner balloon layer 120. A cavity 130 formed by the inner balloon layer 110 and outer balloon layer 120 includes an access tube 170 for injecting a gas or a fluid into the cavity 130 to expand the balloon speculum 100. The access tube 170 may be a flexible tube. For simplicity, the figures depict a short access tube 170, but the flexible tube may extend to a length varying from the diameter of the speculum to several meters.

The speculum 100 has a proximal end 150 and a distal end 160. The distal end 160 may be inserted into a patient's vaginal canal until it comes into contact with or is in close proximity to a patient's cervix. When expanded, as shown in FIG. 2, the speculum 100 forms a tube shaped lumen 140 through which a health care provider may view a patient's cervix, for example. In addition, a healthcare provider may insert tools for treatment into the lumen 140, from the proximal end 150 (proximal to the healthcare provider upon insertion into the patient's vaginal canal) to the distal end 160, for a procedure on, for example, a patient's cervix.

Figure 3:
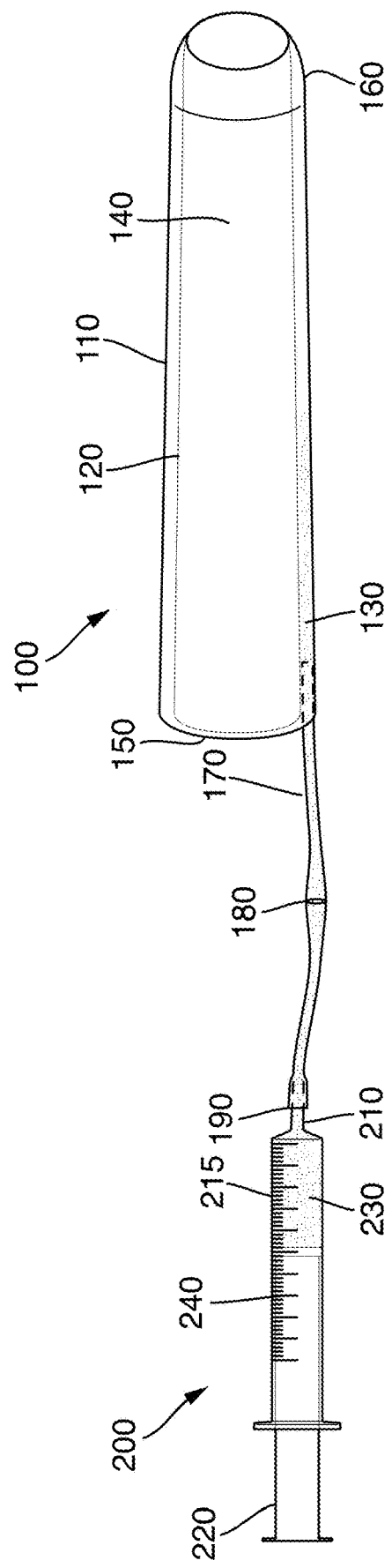
FIG. 3 depicts an expandable balloon speculum with a syringe for inserting fluid into a tube insertion site of the expandable balloon speculum.

FIG. 3 depicts the expandable balloon speculum 100 of FIG. 2, with a syringe 200 for inserting fluid into a tube insertion site of the expandable balloon speculum 100. As discussed with respect to FIG. 2, the speculum 100 includes an outer balloon layer 110, an inner balloon layer 120, and a cavity 130 between the inner balloon layer 120 and the outer balloon layer 110. A fluid may be injected into the cavity 130 via the access tube 170. The expanded balloon speculum 100 forms a tubular lumen 140, through which a health provider may view, for example, a patient's cervix at the distal end of the lumen 140. A valve 180 controls the flow of fluid from the syringe 200 through the access tube 170 into the cavity 130. The syringe 200 expels fluid from the syringe tip 210, into the insertion end 190 of the access tube 170. The syringe body 215 receives a plunger 220, that, when depressed, pushes fluid out of the syringe liquid cavity 230. The syringe body 215 may include volume markings 240. The fluid injected from the syringe 200 into the speculum 100 may be water, saline, a chemiluminescent fluid, air, or another liquid, gas, or gel-like substance.

Chemiluminescence is the emission of light as the result of a chemical reaction. When chemiluminescent (CI) fluids combine, the ensuing reactions emit light. In various embodiments, the CI fluid reactions generate little heat, to avoid heating the speculum and vaginal canal. The combined fluids or solutions may be separated until light is desired, at which time they are mixed to form a chemical reaction that produces light.

In various embodiments, the first solution is luminol, and the second solution is hydrogen peroxide. In various embodiments, the first solution is (9,10-diphenylanthracene (blue) dissolved in diethyl phthalate, rubrene (5,6,11,12-tetraphenyltetracene; yellow) dissolved in diethyl phthalate, or a mixture (50:50 or otherwise) of 9,10-diphenylanthracene and rubrene (white) dissolved in diethyl phthalate, as well as bis (2,4,6-trichlorophenyl) oxalate, and sodium acetate, and the second solution is hydrogen peroxide. In various embodiments, the first solution is luminol (blue), sodium carbonate, copper sulfate, and ammonium carbonate, and the second solution is hydrogen peroxide.

In various other embodiments, the first solution could be any combination of luminol and its derivatives, aridinium esters (for example, lucigenin), anthracene or its derivatives, indoles, polydimethylaminoethylenes, Schiff bases, peroxyoxalates, fluorophores (polycyclic aromatic hydrocarbons), derivative compounds with fluorophores, permanganates, hypochlorites, or iodates, including just one or any number of these components. In various embodiments, the solutions could be aqueous, organic, or a mixture, such as an emulsion. In other embodiments, the solutions could contain colloidal particles, such as nanoparticles.

Several different mechanisms may be employed to store and mix the solutions, before inserting them into the syringe. Alternatively, an additional component, such as a rod or glow stick, could be used as a light source. A glass tube within a plastic tube may be broken, without breaking the plastic tube, by bending the plastic tube containing the glass tube enough to break the glass, but without breaking the plastic tube. This would cause a first solution stored in the glass tube to mix with the second solution stored in the plastic tube, causing a reaction that emits light when the two solutions mix.

Another storing and mixing mechanism uses two balloons, one inside the other, for which the interior balloon is smaller, thinner, and/or weaker than the exterior balloon. For example, the interior balloon may have thinner walls and/or be tightly filled. Distortion of the balloons may cause the interior balloon to rupture, while leaving the exterior balloon intact. This would cause the two solutions, stored in the interior and exterior balloons, respectively, to mix, causing a reaction that emits light.

Another storing and mixing mechanism may include a receptacle with a septum that allows injection of the two solutions into a cavity, so that the previously separate solutions mix and cause a reaction that emits light.

In various embodiments, a chemiluminescent effect may be generated by an electric current, or ultrasonic stimulation, to solutions that emit light in the presence of electric current or ultrasonic stimulation.

FIGS. 4A-4D illustrate placement of shape memory alloy mesh layer. A shape memory alloy, such as the nickel titanium alloy nitinol, may be formed into a mesh, bars, or a skeletal structure. Shape memory alloys, such as nitinol, exhibit a shape memory effect, and has superelastic properties. The shape memory effect is the ability to undergo deformation at one temperature, and then recover its original, undeformed shape upon heating above a transition temperature. The transition temperature of nitinol varies depending on the composition of the alloy. For example, temperatures between about 30° C. (86° F.) and about 130° C. (266° F.) are possible. For specula, a transition temperature between about 30° C. (86° F.) and body temperature, about 37° C. (98.6° F.), may be used. Superelasticity occurs at a narrow temperature range above the transition temperature, so that further heating is not necessary to cause the undeformed shape to recover its shape. Nitinol exhibits elasticity that is an order of magnitude greater than that of ordinary metal.

There are a variety of alloys with shape memory effects. They include Ag—Cd 44/49 at. % Cd, Au—Cd 46.5/50 at. % Cd, Co—Ni—Al, Co—Ni—Ga, Cu—Al—Ni 14/14.5 wt. % Al, 3/4.5 wt. % Ni, Cu—Al—Ni—Hf, Cu—Sn approx. 15 at. % Sn, Cu—Zn 38.5/41.5 wt. % Zn, Cu—Zn—X (X=Si, Al, Sn), Fe—Mn—Si, Fe—Pt approx. 25 at. % Pt, Mn—Cu 5/35 at. % Cu, Ni—Fe—Ga, Ni—Ti approx. 55-60 wt. % Ni, Ni—Ti—Hf, Ni—Ti—Pd, Ni—Mn—Ga, and Ti—Nb. While the examples herein refer to nitinol, other alloys that exhibit shape memory effects may be used.

Figure 4A:
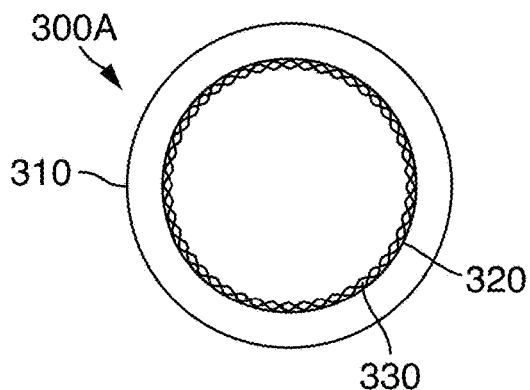
FIGS. 4A-4D illustrate that in various embodiments, the shape memory alloy mesh layer may be interior to the inner balloon layer, as shown in FIG. 4A, between the inner and outer balloon layers abutting the inner balloon layer, as shown in FIG. 4B, between the inner and outer balloon layers abutting the outer balloon layer, as shown in FIG. 4C, or between the inner and outer balloon layers without abutting either the inner or outer balloon layers, as shown in FIG. 4D, as follows.

FIG. 4A is a cross section of an expandable balloon speculum 300A with an outer balloon layer 310 surrounding an inner balloon layer 320. The inner balloon layer 320 surrounds and abuts a shape memory alloy mesh layer 330.

Figure 4B:
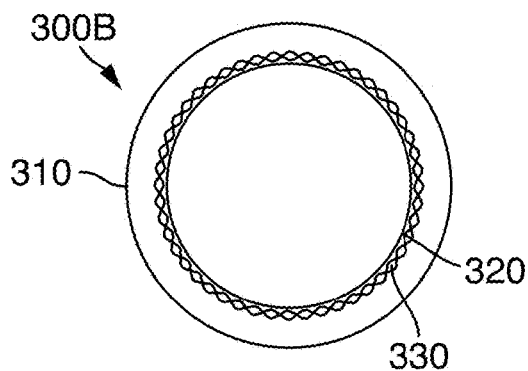

FIG. 4B is a cross section of an expandable balloon speculum 300B with an outer balloon layer 310 surrounding a shape memory alloy mesh layer 330. The shape memory alloy mesh layer 330 surrounds and abuts the inner balloon layer 320.

Figure 4C:
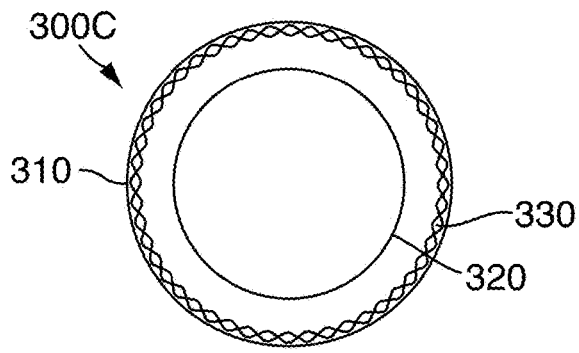

FIG. 4C is a cross section of an expandable balloon speculum 300C with an outer balloon layer 310 abutting and surrounding a shape memory alloy mesh layer 330. The shape memory alloy mesh layer 330 surrounds an inner balloon layer 320.

Figure 4D:
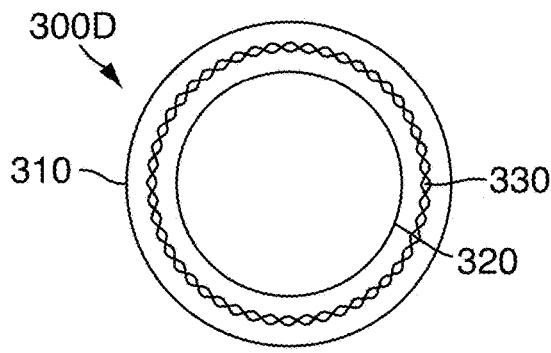

FIG. 4D is a cross section of an expandable balloon speculum 300D with an outer balloon layer 310 surrounding a shape memory alloy mesh layer 330. The shape memory alloy mesh layer 330 surrounds the inner balloon layer 320. The shape memory alloy mesh layer 330 is between, but does not abut, either the inner balloon layer 320 or the outer balloon layer 310.

Figure 5:
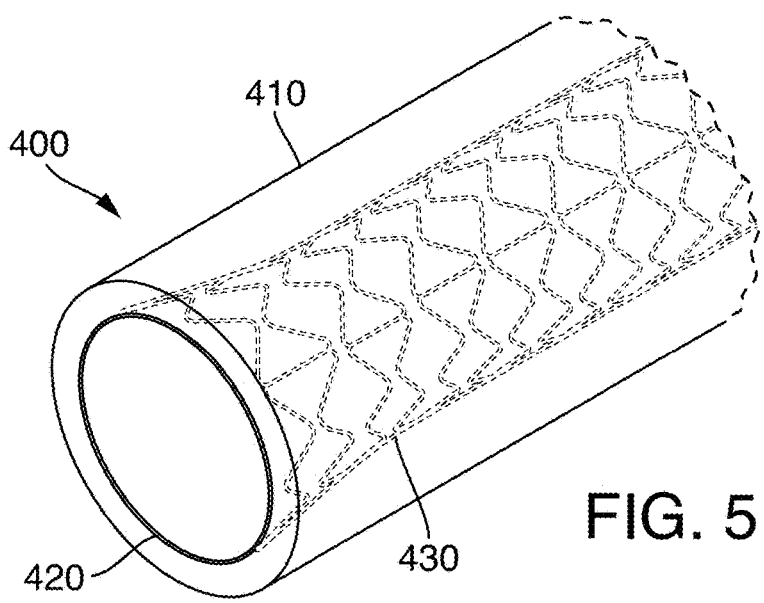
FIG. 5 is a perspective of a speculum showing a flared shape metal alloy mesh. The mesh may be incorporated in specula with cross sections corresponding to FIGS. 4A, 4B, 4C, and 4D. For clarity.

FIG. 5 is a perspective view of a speculum 400 showing a flared shape memory alloy mesh 430, with outer balloon layer 410, and inner balloon layer 420. The shape memory alloy mesh 430 may be incorporated in specula with cross sections corresponding to FIGS. 4A, 4B, 4C, and 4D. For clarity, FIG. 5 illustrates a speculum 400 with a cross section corresponding to FIG. 4B, since the shape memory alloy mesh layer 430 would be further obscured in perspectives of specula corresponding to the cross sections of FIGS. 4A, 4C, and 4D by the inner balloon layer 420.

Figure 6:
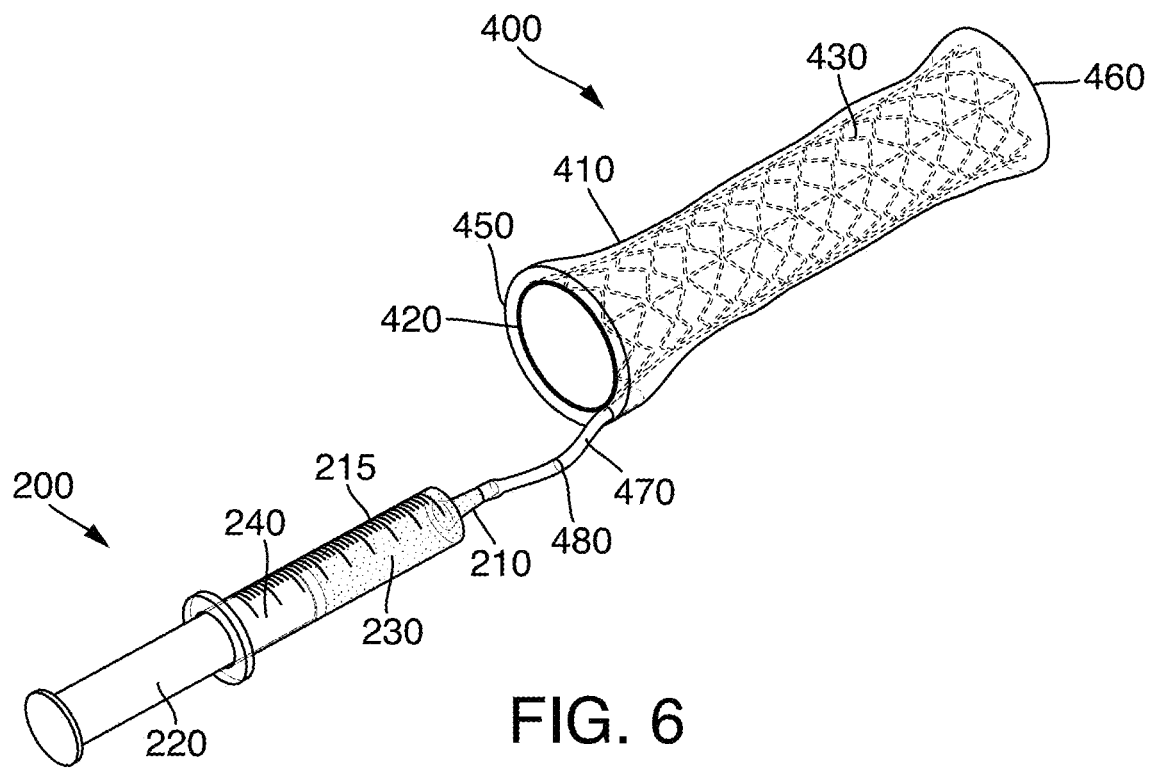
FIG. 6 is a perspective of the speculum of FIG. 5 before pumping in fluid from a syringe.

FIG. 6 is a perspective view of the speculum 400 of FIG. 5, with shape memory alloy mesh layer 430, before pumping in fluid from a syringe 200. The outer balloon layer 410 is not extended, as fluid has not yet been pumped from the syringe 200 to the speculum 400 via access tube 470 between the outer ball layer 410 and the inner balloon layer 420.

A valve 480 may be opened to allow fluid to flow from the syringe 200 to the speculum 400. The speculum 400 has a proximal end 450 and a distal end 460. The syringe 200 expels fluid from the syringe tip 210, into the insertion end of the access tube 170. The syringe body 215 receives a plunger 220, that, when depressed, pushes fluid out of the syringe liquid cavity 230. The syringe body 215 may include volume markings 240. The fluid injected from the syringe 200 into the speculum 100 may be water, saline, a chemiluminescent fluid, air, or another liquid, gas, or gel-like substance.

Figure 7:
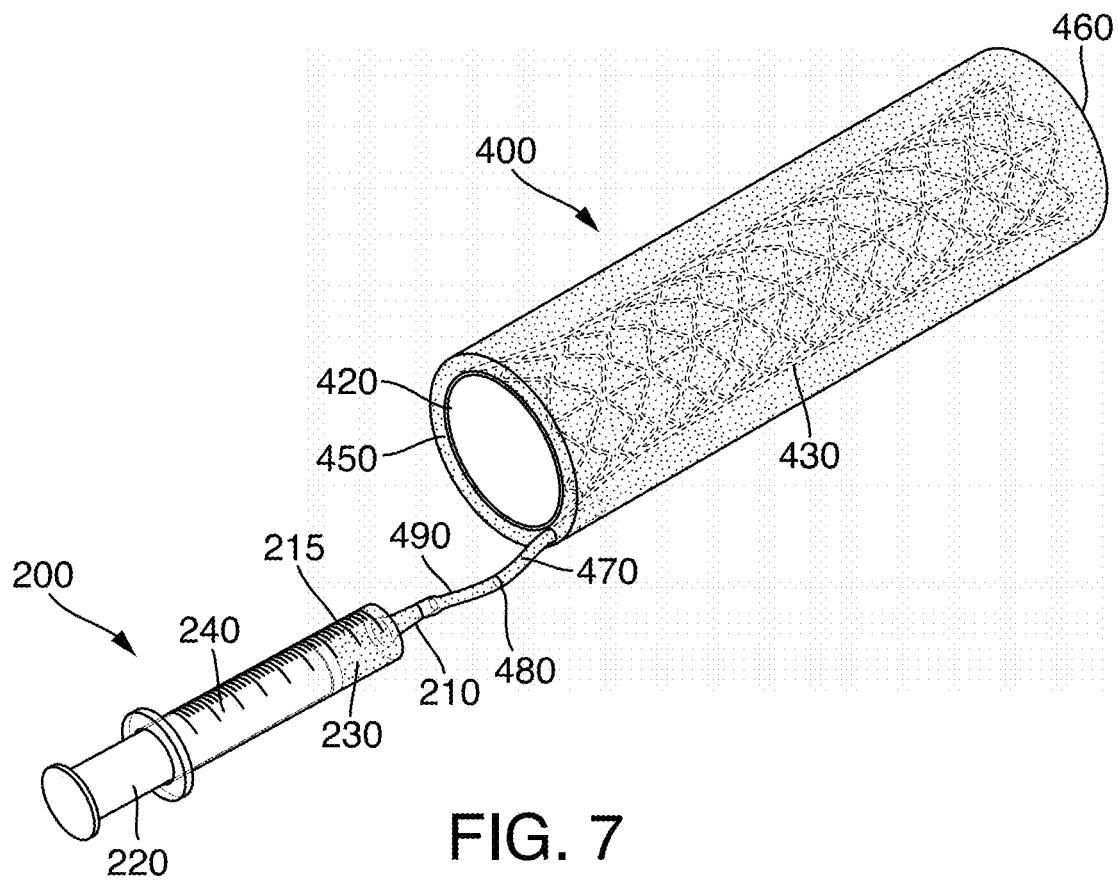
FIG. 7 is a perspective of the speculum of FIG. 6 after pumping in fluid from the syringe. The expansion may occur because of heat expansion of the shape memory alloy, insertion of the fluid, or some combination of the heat expansion of the shape memory alloy and the inserted fluid.

FIG. 7 is a perspective view of the speculum 400 of FIG. 6 after pumping in fluid 230 from the syringe 200. The expansion of the speculum 400 may occur because of heat expansion of the shape memory alloy 430 in addition to the insertion of the fluid. In various embodiments, the fluid is a chemiluminescent fluid that emits light to illuminate at least a portion of a patient's vaginal canal, such as her cervix, near the distal end 460 of the speculum 400.

A valve 480 may be opened to allow fluid to flow from the syringe 200 to the speculum 400. The speculum 400 has a proximal end 450 and a distal end 460. The syringe 200 expels fluid from the syringe tip 210, into the insertion end 490 of the access tube 170. The syringe body 215 receives a plunger 220, that, when depressed, pushes fluid out of the syringe liquid cavity 230. The syringe body 215 may include volume markings 240. The fluid injected from the syringe 200 into the speculum 100 may be water, saline, a chemiluminescent fluid, air, or another liquid, gas, or gel-like substance.

Figure 8A:
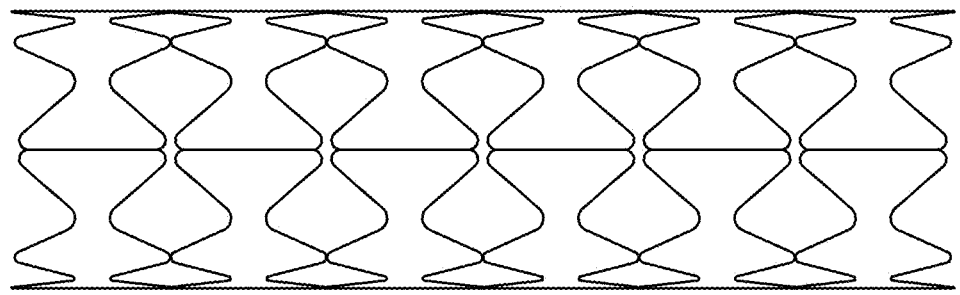
FIG. 8A illustrates an example of shape memory alloy mesh.

FIG. 8A illustrates an example of shape memory alloy mesh 800A. The shape memory alloy may be formed of nitinol, or another shape memory alloy.

Figure 8B:
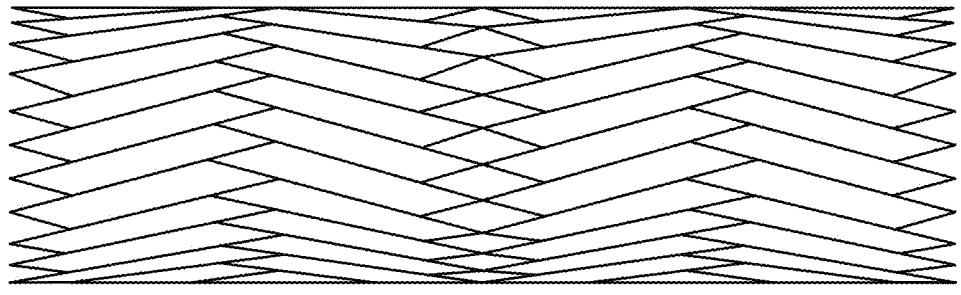
FIG. 8B illustrates another example of a shape memory alloy mesh. Various implementations may include the mesh structure of FIG. 8A, the mesh structure of FIG. 8B, or another mesh structure.

FIG. 8B illustrates another example of a shape memory alloy mesh 800B. Various implementations may include the mesh structure of FIG. 8A, the mesh structure of FIG. 8B, or another mesh structure.

The examples herein describe specula for viewing out of the distal end to examine and/or treat a patient through the distal end of the lumen formed by the speculum. In various embodiments, the distal end of the speculum flares out, for a wider viewing angle of, for example, a patient's cervix. Similarly, the proximal end of the speculum may be flared out to allow for insertion of and manipulation of instruments that are inserted into the lumen of the speculum, through the length of the speculum, towards the distal end of the speculum. The disclosed technology may also be applied to other medical devices, such as anoscopes or colonoscopes. For these devices, a health care provider may need to examine a patient lateral to the direction of travel of the anoscope or colonoscope, through the walls of the anoscope or colonoscope instead of just through the distal end. For example, the walls of the medical device may be clear or translucent, or they may have gaps or windows for viewing. For the case of a colonoscope, this would allow for observation of the colon walls during a colonoscopy.

Unless defined otherwise, all technical and scientific terms used herein have the same meaning as commonly understood by one of ordinary skill in the art to which this invention belongs. In this specification and in the claims that follow, reference will be made to a number of terms that shall be defined to have the following meanings:

The terminology used herein is for the purpose of describing particular embodiments only and is not intended to be limiting of the invention. As used herein, the singular forms "a", "an" and "the" are intended to include the plural forms as well, unless the context clearly indicates otherwise.

"Optional" or "optionally" means that the subsequently described event or circumstance can or cannot occur, and that the description includes instances where the event or circumstance occurs and instances where it does not.

The term "about" when used before a numerical designation, e.g., temperature, time, amount, concentration, and such other, including a range, indicates approximations which may vary by (+) or (−) 10%, 5%, 1%, or any subrange or subvalue there between. Preferably, the term "about" when used with regard to a dose amount means that the dose may vary by +/−10%.

"Comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

It should be noted that any ordering of method steps implied by the drawings or description herein is not to be construed as limiting the disclosed methods to performing the steps in that order. Rather, the various steps of each of the methods disclosed herein can be performed in any of a variety of sequences. In addition, as the described methods are merely exemplary embodiments, various other methods that include additional steps or include fewer steps are also within the scope of the present disclosure.

Although the invention has been described by reference to specific embodiments, it should be understood that numerous changes may be made within the spirit and scope of the inventive concepts described. Accordingly, it is intended that the invention not be limited to the described embodiments, but that it have the full scope defined by the language of the following claims.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The implementations set forth in the foregoing description do not represent all implementations consistent with the subject matter described herein. Instead, they are merely some examples consistent with aspects related to the described subject matter. Although a few variations have been described in detail herein, other modifications or additions are possible. In particular, further features and/or variations can be provided in addition to those set forth herein. For example, the implementations described above can be directed to various combinations and sub-combinations of the disclosed features and/or combinations and sub-combinations of one or more features further to those disclosed herein. In addition, the logic flows depicted in the accompanying figures and/or described herein do not necessarily require the particular order shown, or sequential order, to achieve desirable results. The scope of the following claims may include other implementations or embodiments.

What is claimed is:

1. A speculum, comprising:
   an outer balloon layer;
   an inner balloon layer formed within the outer balloon layer, the outer balloon layer and the inner balloon layer forming a sealed cavity therebetween, at least a portion of the inner balloon layer translucent;
   a chemiluminescent liquid comprising a combination of a first solution and a second solution, the combination of the first and second solutions causing a light-emitting chemical reaction, wherein the sealed cavity is configured to hold the chemiluminescent liquid;
   an access tube for injecting the chemiluminescent liquid into the cavity, the outer balloon layer configured to expand circumferentially in response to the injecting of the chemiluminescent liquid into the cavity; and
   a shape memory alloy layer comprising a mesh continuously circumferentially surrounding the inner balloon layer, the shape memory alloy layer between the inner balloon layer and the outer balloon layer in the sealed cavity, the shape memory alloy layer completely not abutting the inner balloon layer, the shape memory alloy layer completely not abutting the outer balloon layer, the shape memory alloy layer configured to transition to a first shape when heated above a transition temperature.

2. The speculum of claim 1, wherein the shape memory alloy comprises nitinol.

3. The speculum of claim 1, wherein the inner balloon layer has a more rigid structure than the outer balloon layer.

4. The speculum of claim 1, wherein the outer balloon layer comprises latex, rubber, silicon, or a flexible plastic.

5. The speculum of claim 1, further comprising rods incorporated into the outer balloon layer in a longitudinal direction, the rods being flexible.

6. The speculum of claim 5, wherein the rods comprise silicon.

7. The speculum of claim 1, wherein the outer balloon layer surrounds the shape memory alloy layer.

8. A system comprising the speculum of claim 1 and an applicator, wherein the applicator is configured to insert the speculum into a vaginal canal.

9. The speculum of claim 1, further comprising a valve to regulate a flow of fluid from a syringe into the access tube.

10. The speculum of claim 1, wherein the inner balloon layer forms a tube shaped lumen.

11. The speculum of claim 1, wherein the first solution comprises at least one of luminol, sodium carbonate, copper sulfate, and ammonium carbonate, and wherein the second solution comprises hydrogen peroxide.

12. The speculum of claim 1, further comprising:
    a glass tube containing the first solution, and
    a plastic tube containing the second solution and the glass tube, wherein bending the plastic tube containing the glass tube breaks the glass tube without breaking the plastic tube, wherein breaking the glass tube causes the light-emitting chemical reaction in response to a mixing of the first and second solutions.

13. The speculum of claim 1, further comprising:
    an interior balloon containing the first solution, and
    an exterior balloon containing the second solution and the interior balloon, wherein distortion of the exterior balloon containing the interior balloon breaks the interior balloon without breaking the exterior balloon, wherein breaking the interior balloon causes the light-emitting chemical reaction in response to a mixing of the first and second solutions.

14. The speculum of claim 1, further comprising a receptacle with a septum separating the first solution from the second solution, the receptacle and septum configured to allow injection of the first and second solutions into a cavity, wherein the injection of the first and second solutions into the cavity causes the light-emitting chemical reaction in response to a mixing of the first and second solutions.

15. The speculum of claim 1, wherein the chemiluminescent liquid emits light in response to an electric current.

16. The speculum of claim 1, wherein the chemiluminescent liquid emits light in response to ultrasonic stimulation.

* * * * *